United States Patent
Imamura

(10) Patent No.: US 7,021,155 B2
(45) Date of Patent: Apr. 4, 2006

(54) UNIVERSAL MATERIAL TESTING METHOD AND DEVICE THEREFOR

(75) Inventor: Senji Imamura, Chiyoda-ku (JP)

(73) Assignee: Nihon University School Juridical Person, Tokyo (JP)

( * ) Notice: Subject to any disclaimer, the term of this patent is extended or adjusted under 35 U.S.C. 154(b) by 0 days.

(21) Appl. No.: 10/478,924

(22) PCT Filed: May 29, 2002

(86) PCT No.: PCT/JP02/05208

§ 371 (c)(1),
(2), (4) Date: Nov. 25, 2003

(87) PCT Pub. No.: WO02/097399

PCT Pub. Date: Dec. 5, 2002

(65) Prior Publication Data

US 2004/0144180 A1 Jul. 29, 2004

(30) Foreign Application Priority Data

May 31, 2001 (JP) .............................. 2001-165180

(51) Int. Cl.
*G01N 3/00* (2006.01)
(52) U.S. Cl. ...................................................... 73/797
(58) Field of Classification Search ................ 73/788, 73/789, 790, 794, 796, 797, 798, 760
See application file for complete search history.

(56) References Cited

U.S. PATENT DOCUMENTS

| | | | | |
|---|---|---|---|---|
| 3,586,963 A | * | 6/1971 | Arrott et al. ................. | 324/243 |
| 4,222,267 A | * | 9/1980 | Aldrich ..................... | 73/304 C |
| 4,480,482 A | * | 11/1984 | Henry et al. .................. | 73/805 |
| 4,918,993 A | * | 4/1990 | Hughson ..................... | 73/801 |
| 5,156,053 A | * | 10/1992 | Shiraishi et al. .............. | 73/849 |
| 5,193,395 A | * | 3/1993 | Chern et al. .................. | 73/779 |
| 5,305,634 A | * | 4/1994 | Suga et al. .................... | 73/86 |
| 6,205,863 B1 | * | 3/2001 | Ishii et al. .................... | 73/805 |

FOREIGN PATENT DOCUMENTS

| | | |
|---|---|---|
| JP | 64-53128 A | 3/1989 |
| JP | 64-53129 A | 3/1989 |

\* cited by examiner

*Primary Examiner*—Max Noori
(74) *Attorney, Agent, or Firm*—Pearne & Gordon LLP

(57) ABSTRACT

A load increasing in a stepped manner from an initial load is applied to a test piece (4) of material in order to examine mechanical properties of the material by applied load, but the load having a next step load added thereto is applied to the test piece after it is confirmed that the variation of strain within a unit time applied to the test piece in the load (Wn) applied in each step falls within a predetermined value whereby there are measured physical variation and time variation in the load applied in each step. The load applied to the test piece is preferably kept at a constant value and the applied load (Wn) and and time variation are preferably recorded.

4 Claims, 4 Drawing Sheets

FIG. 3

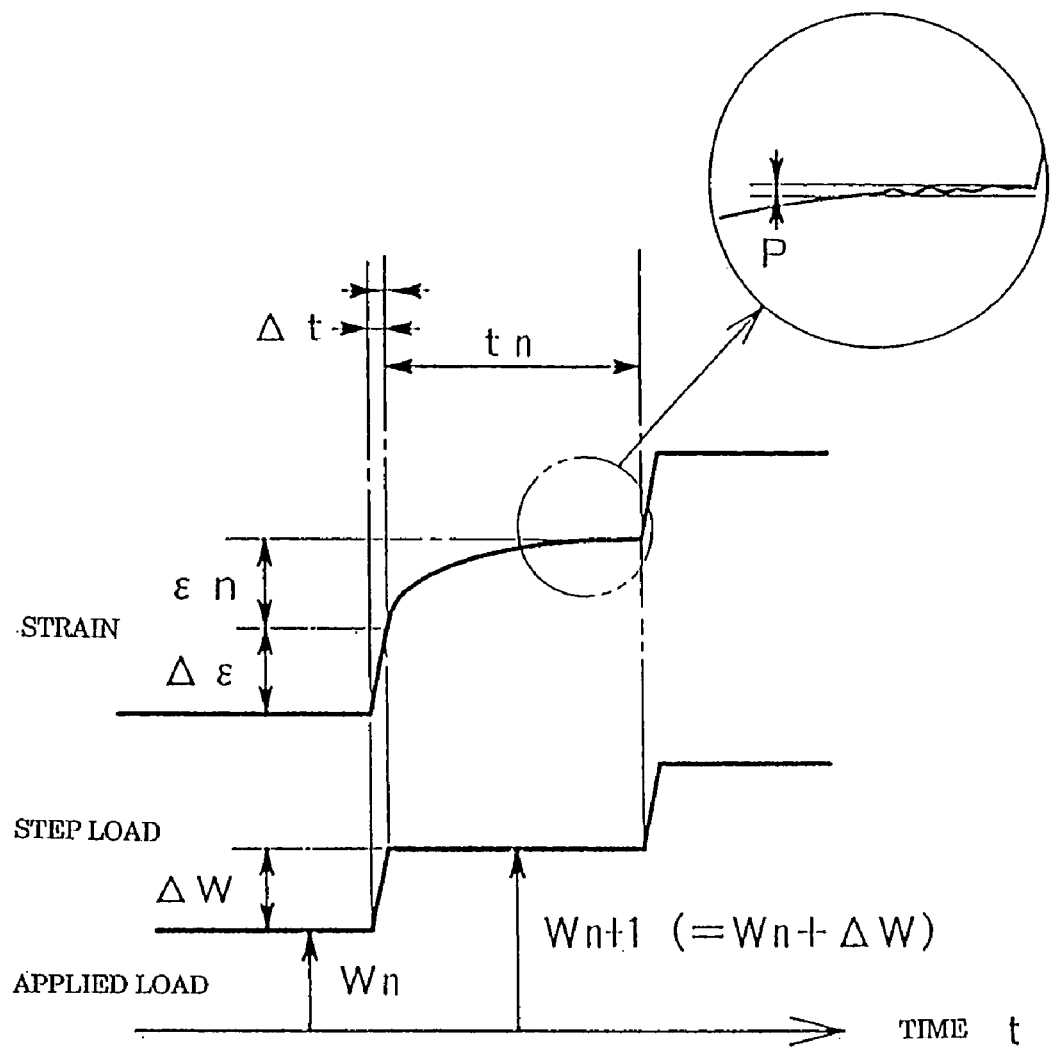

$\Delta W$ :  STEP LOAD $\Delta \varepsilon$ :  STRAIN VARIATION JUST AFTER APPLICATION OF Nth APPLIED LOAD $\varepsilon n$ :  STRAIN VARIATION FROM APPLICATION OF Nth APPLIED LOAD UNTIL STABILIZATION THEREOF $\Delta t$ :  TIME IN WHICH Nth LOAD IS APPLIED $t n$ :  TIME REQUIRED FOR STABILIZATION OF STRAIN BY Nth APPLIED LOAD $P$ :  VALUE OF ALLOWANCE RANGE OF DIFFERENCE BETWEEN FIRST AND LAST STRAINS

UNIVERSAL MATERIAL TESTING METHOD AND DEVICE THEREFOR

TECHNICAL FIELD

This invention relates to a universal material test method used for evaluating physical properties of an objective material by loading tension, compression, bending etc. to a test piece of the objective material and an apparatus for carrying out the test method.

BACKGROUND OF THE INVENTION

Describing a tension tester as an example of a test machine used for the universal material test, this tension tester 1 is shown in FIG. 1 and comprises a base 10, a gate-shaped support frame 11 disposed on an upper face of the base 10 and opened on its front and rear sides, upper and lower chucks 12 and 13 provided at upper and lower positions of the base 10, respectively to grapes the test piece 4 and a load mechanism 2 for tension load provided on one of the chucks, which is the upper chuck 12 in the illustrated example through a load cell 14, for example. The other chuck, which is the lower chuck 13 in the illustrated example, is securely attached to the base 10.

The load mechanism for tension load comprises a servo motor 21 disposed below the base 10, two ball screws 18 contained in the support frame 11 on both sides there and rotated by the servo motor 21 and a crosshead 17 meshed with the ball screws 18 and moved in upward and downward directions by rotation of the ball screws 18. The upper chuck 12 is suspended from and supported by the crosshead 17 through the load cell 14. Thus, as the crosshead 17 vertically moves in the upward and downward directions, tension load is applied to the test piece 4 and the actual tension load applied to the test piece 4 is detected by information from the load cell 14.

In a conventional material test method using such an apparatus, the tension load is applied to the test piece with predetermined speed (a crosshead speed of 0.1 mm/min., for example) until it reaches the load assumed to reach a break point of the test material (500 N through 300 KN, for example) and variation in strain $\varepsilon$ while the tension load is being applied to the test material is subsequently measured to obtain a yield point and the break point of the test material, for example.

The technique of testing the material by applying the predetermined load to the test material at the suitably set up speed is a generally common one in the measurement test for specifying the mechanical properties of the material such as the tension test, the compression test and the bending test and continues from former times to present times.

The aforementioned conventional technique can obtain the general strain, the yield point, the break point and so on of the test piece, but its principal object is that the load such as tension, compression etc. is continuously applied to the test piece at the preset speed until the objective phenomena (the break, for example) appears and there has been not noticed variation in the true strain occurring in the test piece when certain load is applied thereto. In other words, for example, in the measurement of the yield point where plastic deformation of the material starts, there appears the phenomena that the strain is slowly advancing in long time under the fixed load and therefore in the conventional measurement depending on the tension speed, the measurement is made in the state where the strain is still advancing and in an unstable condition. Thus, the next load is applied to the test piece before the strain beginning to occur at certain load point stops, which causes the problem of the reliability of the measurement value and the basis thereof.

Therefore, there are some cases where the same material would have various strain speeds depending on the set tension speed (the speed corresponding to the movement speed of the crosshead, in the aforementioned example) and would have different strain speed depending on the applied load. In the conventional test method having such a viewpoint not aimed, there is a problem in which the true mechanical properties of the material have not been obtained.

Since the test apparatus for carrying out the aforementioned conventional test method has not been designed from such a viewpoint, an operator can work only paying attention to what speed at which the load should be applied to the test piece, how correctly the strain should be measured or how correctly the yield point and the break point should be measured. Even though the computer technology, which has accomplished a remarkable development in recent years, is used, the precision and the automation of the measurement have been just asked for without having gotten out of the conventional measurement viewpoint.

The object of the invention is to provide a universal material test method and a test apparatus suitable for carrying out this test method adapted to be able to judge the property or the treatment process of a material by measuring a time in which the strain of the material gets stable under a new viewpoint that strain of the material varies on change of the component of the material and change of organization of the material when it is treated and especially thermally treated when constant load is applied to the material, which fundamentally changes from the point view of the prior art material test method.

DISCLOSURE OF THE INVENTION

This invention provides a universal material test method and an apparatus therefor having the following features in order to accomplish the aforementioned object.

More particularly, the universal material test method of the invention is the method of testing mechanical properties of an objective material by measuring a change in the load by applying tension, compression, bending etc. to a test piece of the objective material in which the load increasing from a set-up initial load in a stepped manner is applied to the test piece and characterized in that the load having a next step load added thereto is applied to the test piece after it is confirmed that the variation of the strain within a unit time applied to the test piece in the load applied in each step falls within a predetermined value whereby physical variation and time variation in the load applied in each step is measured.

An apparatus for carrying out the test method of the invention is characterized by comprising a loading mechanism (2) to apply a load to a test piece (4), detection means (5) to detect a deformation of the test piece (4), judgment means (J) to judge that a variation of strain of the test piece within the unit time when the load is applied falls within a predetermined value on the information from the detection means (5) and load control means to instruct the loading mechanism to further add a step load of predetermined value after the judgment means (J) judges that the variation of the strain of the test piece within the unit time falls within the predetermined value.

There may be used the loading mechanism (2), which can apply the step load to the test piece in the stepped manner. For instance, there may be used means to sequentially accumulate a weight of predetermined load, but in order to mechanically practice this, there may be desirably used constant load control means (C) to maintain a uniform value of the load applied to the test piece (4).

The apparatus of the invention may comprise record means to record the load (Wn) of each step and the physical variation and the time variation thereof for the purpose of analyzing the measured data later.

The test method of the invention continues to apply the load (Wn) of constant weight by suspending the weight of predetermined unit value from a lower end of the test piece until the variation of the strain falls within the predetermined value and sequentially apply the load (Wn) having another step load added thereto when it is confirmed that the variation of the strain falls within the predetermined value, which has a procedure substantially different from that of the prior test method and therefore, the inventor calls this "dead weighted loading type universal test method" or "dead weighted loading type universal test machine" whereby it can be distinguished from an oil pressure type, screw type or operating lever type universal test machine of the prior art.

The reference numbers having a parenthesis attached thereto in the claims and the column of means to resolve the problems are conveniently added thereto for more easily understanding the construction of the invention and it should be noted that the construction of the invention is not limited to the form illustrated in the drawings.

BRIEF DESCRIPTION OF THE DRAWINGS

FIG. 3 illustrates a graph showing values measured by the universal material test method according to the embodiment of the invention.

BEST MODE OF CARRYING OUT THE INVENTION

Figure 1:
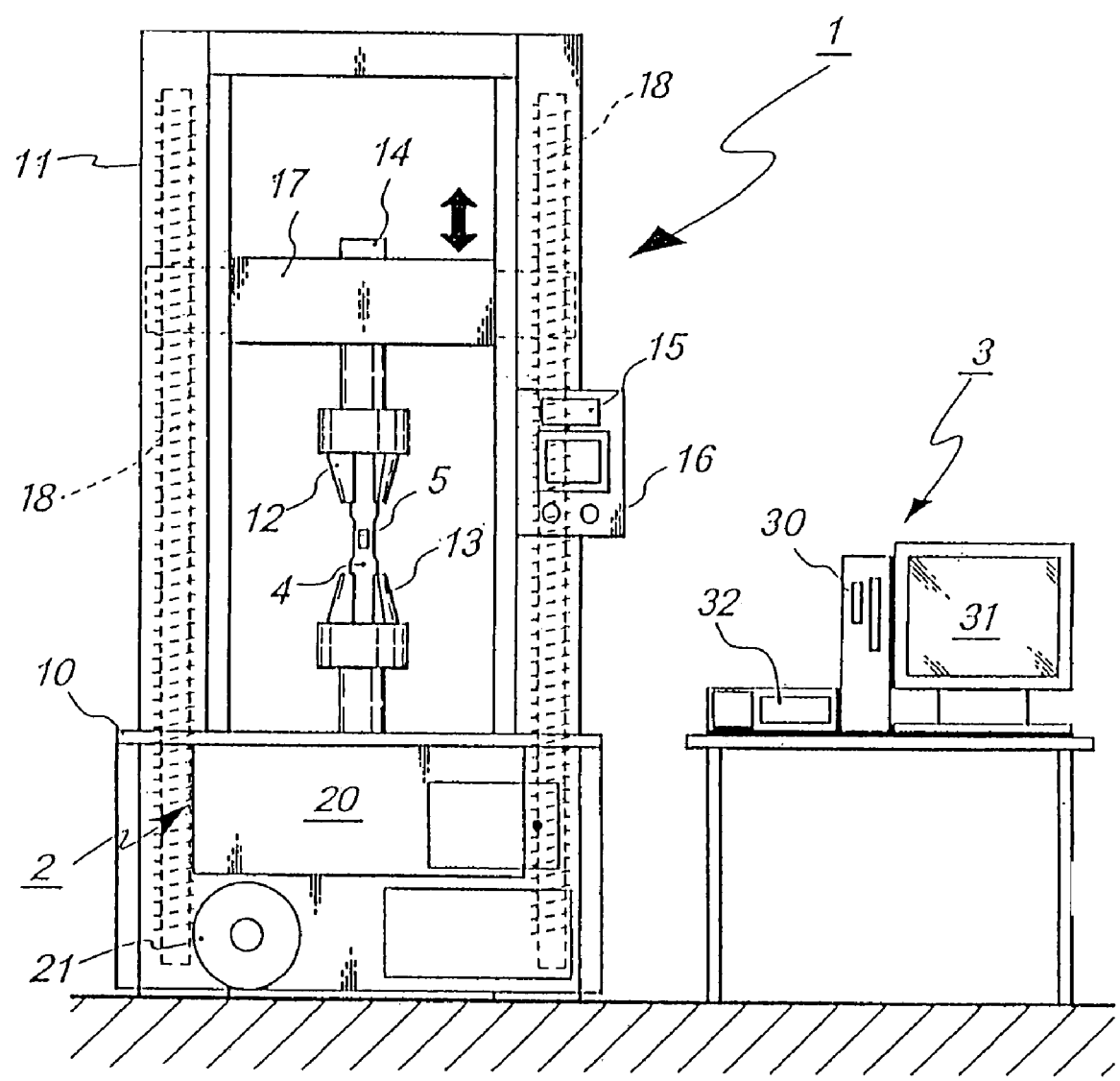
FIG. 1 is a brief front view of a universal material test apparatus constructed in accordance with one embodiment of the invention.

A concrete form of embodiment of the invention will be described and illustrated with reference to the drawings hereinafter.

The test apparatus of the invention can be used as universal material test machine such as a tension test machine, a compression test machine, a bending test machine, etc, but in the present embodiment, it will be explained as the tensile test machine.

The tensile test machine 1 according to the present embodiment may have the construction similar to that of the test machine described with reference to the prior test method and comprises a base 10, a support frame 11, upper and lower chucks 12 and 13, a load cell 14, a crosshead 17, ball screws 18 and a loading mechanism 2.

Onto the support frame 11 are disposed and attached an indicator to indicate initial setting information for arranging the mount of the test piece 4 on the upper and lower chucks 12 and 13 and an operation box 16 to perform the operation thereof. The load mechanism 2 comprises speed change means 20 to upwardly and downwardly move the upper chuck 12 in a vertical direction through the association with the crosshead 17 and the ball screws 18 and a servo motor 21 to supply a fine drive power to the speed change means 20. The servo motor 21 performs "constant load control" to maintain the set load at a constant value and "applied load control" to apply the load having a set step load ($\Delta W$) added thereto. Each of the controls may be performed by a program control using a personal computer 3 and sequential information of the step load, the applied load (Wn), the lapse time etc., are displayed on a display instrument 31 and recorded in record means such as hard disk, flexible disk, etc.

The constant load control means C to perform the "constant load control" among the aforementioned controls is for controlling the set load (100 N, for example) to be always applied to the lower end of the test piece 4. In the load action using the crosshead 17, for example, since an elongation occurs when the test piece 4 is initially tensioned by the load of 100 N and the initial load (100 N) varies, a signal from the load cell 14 is monitored on real time and the load servo motor 21 is controlled to be finely rotated so that the set load (100 N) is always applied to the test piece 4. This means that the same state as the state where the weight is suspended from the lower end of the test piece 4 is accomplished by the mechanical tension of the upper chuck 12. The mechanism itself to accomplish the constant load control means C is the conventional technique.

The applied load control means L to accomplish the "applied load control" among the aforementioned controls is for controlling the load (Wn) having the predetermined step load ($\Delta W$) sequentially added to the set initial load (W1) therefrom to act to the test piece 4. This is performed in accordance with the control flow chart described later.

A strain gauge 5 is disposed between the objective points of the test piece 4 grasped by the upper and lower chucks 12 and 13 and a signal obtained by amplifying the strain $\varepsilon$ of the test piece 4 by a strain meter 32 is fed to the personal computer 3 performing the controls on real time.

Figure 2:
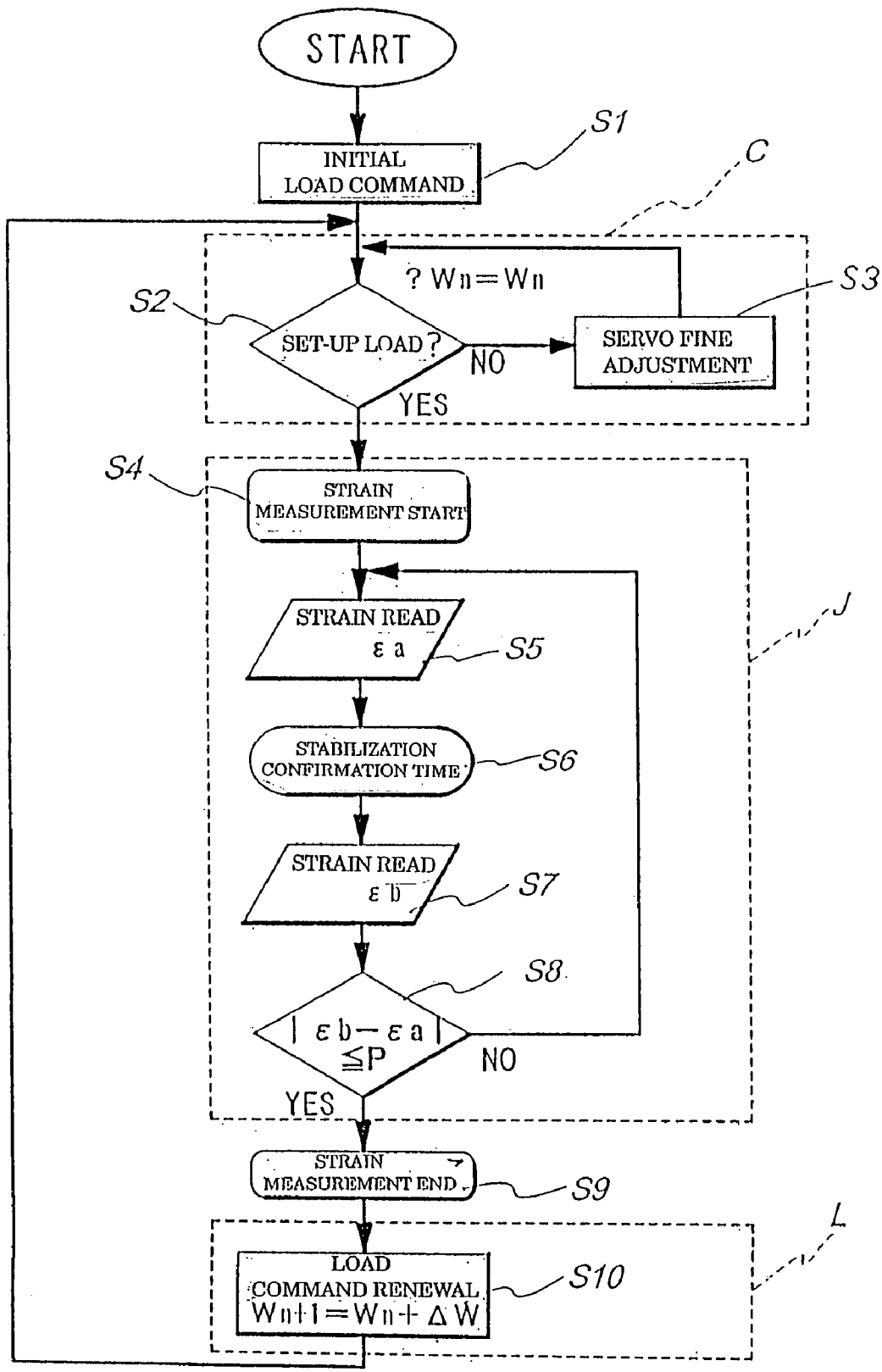
FIG. 2 is a flow chart showing a control of a universal material test method of one embodiment of the invention.

The test method of the embodiment of the invention is realized by controlling the test machine 1 constructed in the aforementioned manner as described later. This will be explained hereinafter on the flow chart shown in FIG. 2.

At first, in the STEP (briefly referred to as just "S" hereinafter) 1, a command to apply to the test piece 4 the initial load W1 to start the measurement is fed to the servomotor 21. The initial load W1 is appropriately set within the resilient range of the test piece 4. A sensor signal from the load cell 14 is monitored so as to be able to maintain the constant initial load W1 (see S2) and the aforementioned servo motor 21 is finely driven in a proper manner in consideration of a variation in the tensile load due to the delicate elongation whereby the load during its application is always kept at a constant value (see S3).

Thereafter, the applied load reaches the aforementioned initial load (W1) and the measurement of strain $\varepsilon$ starts on the output signal from the strain gauge 5 mounted on the test piece 4 while the constant load is maintained by the constant load control means C (see S4). Subsequently, the strain $\varepsilon$ when the measurement starts is once read and recorded (see S5), the strain $\varepsilon$ is again read and recorded (see S7) after predetermined time (10 second, 20 second and so on, for example) lapses (see S6) and whether a difference $\varepsilon$ between the previous and last strains ($=\varepsilon b-\varepsilon a$) falls within the predetermined allowance range P ($|\varepsilon d| \leq P$) or not is judged by the judgment means J (see S8). If the difference between the previous and last strains is out of the predetermined allowance range P (|εd|>P), the procedure is returned to the STEP 5 and the measurement of the strain ε a (see S5), the measurement of the strain ε b (see S7) after the predetermined time (10 second, 20 second and so on, for example) lapses (see S6) and the arithmetical operation of the difference ε d between the previous and last strains are performed and repeated until the difference ε d falls within the predetermined allowance range P(|εd|≦P).

If the difference ε d falls within the predetermined allowance range P(|εd|≦P), it is judged that the advance of the strain in the initial load (W1) substantially stops (see S9) and the lapse time and so on at that time are recorded in the record means (internal or external memory devices). Although the predetermined allowance range P is desirably zero, the tension of the test piece 4 is applied by the aforementioned load mechanism 2 and therefore a little deflection occurs. Thus, waiting until the difference ε d reaches zero is not realistic and therefore the difference ε d converging within the predetermined allowance value P is deemed that the strain advance stops. In the case where the load is applied by suspending the weight, but not by the aforementioned load mechanism 2, the stop of the advance of the strain (P=0) may be judged.

After |εd|≦P is judged, the applied load control means L feeds to the servo motor 21 the load command of the applied load W2 (=W1+ΔW) for the second step having the predetermined step load ΔW added to the initial load W1 (see S10).

Herein, the second step applied load W2 is again maintained at the constant value by the aforementioned constant load control until the advance of the strain stops (including the fictitious stop). When the advance of the strain due to the second step applied load W2 stops, another step load ΔW is added and the operation is repeated. This is the same system as the predetermined weight is suspended from the lower end of the test piece 4 and another weight is added and suspended when the advance of strain stops. The load by the weight is maintained in the state where the constant applied load is always maintained during the application thereof. The aforementioned constant load control means C is used for accomplishing this state by the aforementioned tension mechanism.

In this manner, the next stage applied load Wn+1 (=Wn+ΔW) having the step load ΔW added to the applied load Wn while maintained at the constant value is sequentially applied to the test piece 4 in the stepped manner whereby the strain in each step and the time in which the advance of the strain stops (including the fictitious stop) can be measured.

EXAMPLE OF MEASUREMENT VALUE

Figure 4:
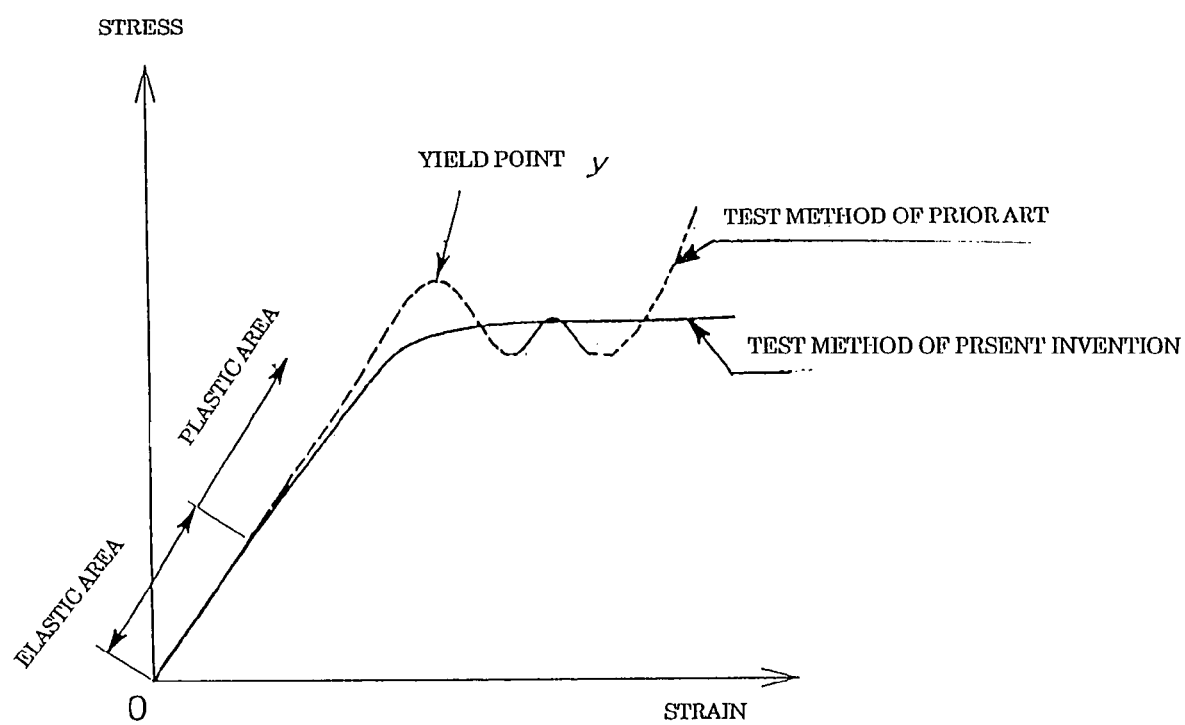
FIG. 4 illustrates a graph showing values measured by the universal material test method according to the embodiment of the invention.

The graphized value measured using the aforementioned test method is as shown in FIGS. 3 and 4.

FIG. 3 shows how the strain varies when the next stage applied load (Wn+1) having the step load ΔW added to the initial load is applied to the test piece and the time Δt in which the step load (ΔW) is applied, the variation of the strain immediately after the step load (ΔW) is applied (the next stage applied load (Wn+1) is applied), the time (tn) in which the strain is stabilized and the variation ε n of the strain which occurs until the difference stably falls within the allowance value P immediately after the next stage applied load is applied are shown in FIG. 3.

FIG. 4 is a graph showing the relationship between stress and strain in the measurement by the test method of the embodiment of the invention and the prior test method. It will be noted from the graph that there appears no phenomena in which the stress slightly decreases at the yield point y, which appears in the prior test method and it will be noted that the strain continues to increase in a natural manner immediately before the test piece is broken.

Although, in the aforementioned embodiment, the strain is measured by the strain gauge 5 adhered to the test piece 4, the strain measurement means is not limited thereto, of course, and there may be used either of contact type and non-contact type sensor means.

With the invention constructed as aforementioned, the following effects can be obtained. When the load is applied to metal material, deformation corresponding to the load never occurs at moment, but it will occur in a certain time and the time required for the deformation depends on materials. Thus, it will be noted that the peculiar action (the relationship between the stress and the time) of the materials can be examined by measuring this time. Since these actions correspond to the variation in the component of the materials, the organization due to their heat treatment and so on, the properties of the materials can be examined by measuring the time for their deformation.

The following can be seen by measuring the time constant. When the stress-strain curve is prepared, it can be expressed so that the singular points (upper yield point and lower yield point) of the phenomena in which the stress slightly decreases at the yield point as shown in the prior art never appear and the strain smoothly increases immediately before the test piece is broken. When the test piece to which the load is once applied nearly until it is broken is again tested in the similar manner, the variation in the strain is different from the previous test.

Furthermore, the component of the materials and the difference due to the method of manufacture can be quantified and the change of the steps of manufacture and the change of the manufacture lots even for the materials of the same component ratio cause the variation in the strain speed, for instance. Thus, the change of the steps of manufacture and the change of the manufacture lots can be judged by patternizing these variations in the strain speed and comparing these patterns.

UTILIZABILITY FOR INDUSTRIES

As aforementioned, the method of the invention can properly evaluate the properties of the objective materials and judging the variation in the step of manufacture and the manufacture lots using the results of the evaluation.

The invention claimed is:

1. A universal material test method for examining mechanical properties of an objective material by measuring deformation with a change in a load applied to a test piece of said objective material in which the load increasing from a set-up initial load in a stepped manner is applied to said test piece and characterized in that the load having a next step load of preselected constant value added thereto is applied to the test piece after it is confirmed that the variation of strain within a unit time resulting from a prior step load of preselected constant value applied to the test piece is stabilized at a predetermined value in each step whereby there are measured physical variation and time variation and the load applied in each step.

2. A universal material test apparatus characterized by comprising a loading mechanism to apply a load to a test piece, detection means to detect a deformation of the test piece, judgment means to judge that a variation of strain of the test piece within a unit time when the load is applied falls within a predetermined value based on information from said detection means and load control means to instruct the loading mechanism to further add a step load of preselected contant value after said judgment means judges that the variation of the strain of the test piece within the unit time is stabilized within the predetermined value.

3. A universal material test apparatus as set forth in claim 2, and further comprising record means to record the load applied in each step, its physical variation and time variation until said variation of strain is stabilized within the predetermined value in each step.

4. A universal material test apparatus as set forth in claim 1, further including the step of examining the measured physical variation, time variation and load applied in each step to evaluate historical properties of the said objective material.

* * * * *